(12) United States Patent
Callaghan

(10) Patent No.: US 9,777,268 B2
(45) Date of Patent: Oct. 3, 2017

(54) METHOD OF IMMOBILISING RNA ONTO A SURFACE

(75) Inventor: Anastasia Jane Callaghan, Portsmouth (GB)

(73) Assignee: UNIVERSITY OF PORTSMOUTH, Portsmouth (GB)

( * ) Notice: Subject to any disclaimer, the term of this patent is extended or adjusted under 35 U.S.C. 154(b) by 201 days.

(21) Appl. No.: 14/116,390

(22) PCT Filed: May 14, 2012

(86) PCT No.: PCT/GB2012/051072
§ 371 (c)(1),
(2), (4) Date: Nov. 8, 2013

(87) PCT Pub. No.: WO2012/156718
PCT Pub. Date: Nov. 22, 2012

(65) Prior Publication Data
US 2014/0087972 A1   Mar. 27, 2014

(30) Foreign Application Priority Data

May 13, 2011   (GB) .................................. 1108041.3

(51) Int. Cl.
*C12Q 1/68* (2006.01)
*C12N 15/10* (2006.01)
*C12N 15/113* (2010.01)

(52) U.S. Cl.
CPC ....... *C12N 15/1093* (2013.01); *C12Q 1/6837* (2013.01)

(58) Field of Classification Search
CPC .......................... C12N 15/1093; C12Q 1/6837
See application file for complete search history.

(56) References Cited

U.S. PATENT DOCUMENTS

2004/0137439 A1    7/2004  Liao et al.
2004/0203085 A1*  10/2004  Bernard et al. ............... 435/7.94
(Continued)

FOREIGN PATENT DOCUMENTS

DE    WO 2010100265 A1 *  9/2010   .......... C12Q 1/6837
WO        9919341 A1       4/1999
(Continued)

OTHER PUBLICATIONS

Srisawat et al. (Methods, 2002, 26:156-161).*
(Continued)

*Primary Examiner* — Jeremy C Flinders
(74) *Attorney, Agent, or Firm* — Cantor Colburn LLP

(57) ABSTRACT

The invention relates to a method of immobilising at least one RNA molecule onto a surface of a support comprising: i) providing a first support having a surface on which at least one DNA molecule is immobilised, wherein the DNA molecule encodes an RNA molecule and the encoded RNA molecule comprises a binding molecule; ii) providing a second support having a surface on which at least one binding partner for interacting with the binding molecule is immobilised; iii) arranging the first and second supports such that the surfaces displaying the immobilised molecules are in close proximity and substantially face each other, and contacting the DNA molecule immobilised on the surface of the first support with transcription reagents; and iv) carrying out a transcription reaction to generate the encoded RNA molecule, wherein the RNA molecule is directly immobilised onto the surface of the second support via an interaction between the binding molecule of the RNA molecule and the binding partner on the surface of the second support.

29 Claims, 3 Drawing Sheets

(56) References Cited

U.S. PATENT DOCUMENTS

Figure 1:
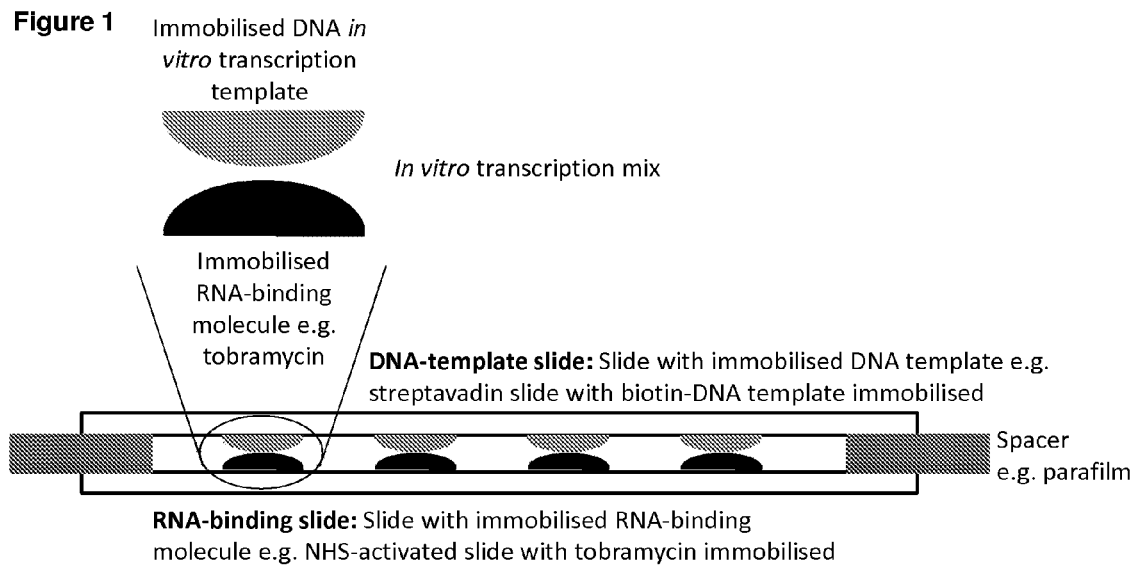

2006/0078889 A1     4/2006    Bhattacharjee et al.
2010/0240544 A1     9/2010    Liu et al.

FOREIGN PATENT DOCUMENTS

WO     2004031366 A2     4/2004
WO     2006112815 A2     10/2006

OTHER PUBLICATIONS

Marble et al. (Biotechnol. Prog., 1995, 11:393-396).*
Collett et al. (Analytical Biochemistry, 2005, 338:113-123).*
He et al. (Nat. Meth., 2008, 5:175-177).*
Gao et al. "Thermodynamically Balanced Inside-out (TBIO) PCR-based Gene Synthesis: A Novel Method of Primer Design for High-fidelity Assembly of Longer Gene Sequences" Nucleic Acids Research, vol. 31, No. 22, e143 (2003; 11 Pages.
Hogg et al., "RNA-based Affinity Purification Reveals 7SK RNPs With Distinct Composition and Regulation" RNA A Publication of the RNA Society; 2007, vol. 13, No. 6: pp. 868-880.
Kim et al. "Transfer of Surface Polymerase Reaction Products to a Secondary Platform with Conversation of Spatial Registration" Journal of American Chemical Society; 2006, 128, pp. 12076-12077.
Lee et al. "Creating Advanced Multifunctional Biosensors with Surface Enzymatic Transformations" Langmuir, Jun. 6, 2006; 22(12); pp. 5241-5250.
International Search Report for International Patent Application No. PCT/GB2012/051072; International Filing Date: May 14, 2013; Date of mailing: Jul. 20, 2012; 3 Pages.
Sendroiu et al., "Ultrasensitive DNA Microarray Biosensing via in Situ RNA Transcription-Based Amplification and Nanoparticle-Enhanced SPR Imaging" Journal of the American Chemical Society; 2011; 133, pp. 4271-4273.
Wahlestedt, "Natural Antisense and Noncoding RNA Transcripts as Potential Drug Targets" Drug Discovery Today, vol. 11, No. 11/12 (2006), pp. 503-508.

* cited by examiner

SEQUENCE LISTING

```
<160> NUMBER OF SEQ ID NOS: 19

<210> SEQ ID NO 1
<211> LENGTH: 25
<212> TYPE: DNA
<213> ORGANISM: Artificial sequence
<220> FEATURE:
<223> OTHER INFORMATION: Primer corresponding to the T7 promoter
      sequence

<400> SEQUENCE: 1
ctcgagtaat acgactcact atagg                                           25

<210> SEQ ID NO 2
<211> LENGTH: 24
<212> TYPE: DNA
<213> ORGANISM: Artificial sequence
<220> FEATURE:
<223> OTHER INFORMATION: Primer complementary to the 3' end of the
      EV71-IRESTobApt sequence

<400> SEQUENCE: 2
agagagggct cagcacgagt gtag                                            24

<210> SEQ ID NO 3
<211> LENGTH: 777
<212> TYPE: DNA
<213> ORGANISM: Artificial sequence
<220> FEATURE:
<223> OTHER INFORMATION: The EV71-IRESTobApt DNA template sequence

<400> SEQUENCE: 3
ctcgagtaat acgactcact atagggagac gatcaatagc aggtgtggca caccagtcat    60
accttgatca agcacttctg tttccccgga ctgagtatca ataggctgct cgcgcggctg   120
aaggagaaaa cgttcgttac ccgaccaact acttcgagaa gcttagtacc accatgaacg   180
aggcagggtg tttcgctcag cacaacccca gtgtagatca ggctgatgag tcactgcaac   240
```

```
ccccatgggc gaccatggca gtggctgcgt tggcggcctg cccatggaga atccatggg      300 acgctctaat tctgacatgg tgtgaagagc ctattgagct agctggtagt cctccggccc     360
ctgaatgcgg ctaatcctaa ctgcggagca catgctcaca aaccagtggg tggtgtgtcg     420
taacgggcaa ctctgcaacg gaaccgacta ctttgggtgt cccgtgtttc cttttattcc     480
tatattggct gcttatggtg acaatcaaaa agttgttacc atatagctat tggattggcc     540
atccggtgtg caacagggca attgtttacc tatttattgg ttttgtacca ttatcactga     600
agtctgtgat cactctcaaa ttcattttga ccctcaacac aatcaaacat gagcacgaat     660
cctaaacctc aaagaaaaac caaacgtaac caaccgtc gcccacaaac ctcgactctt       720
ctagactctc tggcttagta tagcgaggtt tagctacact cgtgctgagc cctctct        777
```

<210> SEQ ID NO 4
<211> LENGTH: 113
<212> TYPE: DNA
<213> ORGANISM: Artificial sequence
<220> FEATURE:
<223> OTHER INFORMATION: HapR DNA template sequence

<400> SEQUENCE: 4

```
ctcgagtaat acgactcact atagggcttt aagtagcaaa taacaaaata atcattagag      60
caaaatgctc aatcaacaac tcaattggca aggatatacc cctatggacg cat            113
```

<210> SEQ ID NO 5
<211> LENGTH: 95
<212> TYPE: DNA
<213> ORGANISM: Artificial sequence
<220> FEATURE:
<223> OTHER INFORMATION: MicAstab DNA template sequence

<400> SEQUENCE: 5

```
ctcgagtaat acgactcact atagaaagac gcgcatttgt tatcatcatc cctgggaaag      60
cgaggctttc cctggccact cacgagtggc ctttt                                 95
```

<210> SEQ ID NO 6
<211> LENGTH: 122
<212> TYPE: DNA
<213> ORGANISM: Artificial sequence
<220> FEATURE:
<223> OTHER INFORMATION: Grr1 DNA template sequence

<400> SEQUENCE: 6

```
ctcgagtaat acgactcact atagggtgac ccgcaagggt cacctagcca actgacgttg      60
ttagtgaata atcaatgttc acaaataaca gccaatagac tcattctatt ggctattttt     120
tt                                                                    122
```

<210> SEQ ID NO 7
<211> LENGTH: 98
<212> TYPE: DNA
<213> ORGANISM: Artificial sequence
<220> FEATURE:
<223> OTHER INFORMATION: MicA DNA template sequence

<400> SEQUENCE: 7

```
ctcgagtaat acgactcact atagggaaaa gacgcgcatt tgttatcatc atccctgaat      60
tcagagatga aattttggcc actcacgagt ggccttttt                             98
```

<210> SEQ ID NO 8
<211> LENGTH: 170

```
<212> TYPE: DNA
<213> ORGANISM: Artificial sequence
<220> FEATURE:
<223> OTHER INFORMATION: HapRTobApt DNA template sequence

<400> SEQUENCE: 8
ctcgagtaat acgactcact atagggcttt aagtagcaaa taacaaaata atcattagag      60
caaaatgctc aatcaacaac tcaattggca aggatatacc cctatggacg cataaaaaaa     120
aaaaaaaaaa aacttagtat agcgaggttt agctacactc gtgctgagcc                170

<210> SEQ ID NO 9
<211> LENGTH: 151
<212> TYPE: DNA
<213> ORGANISM: Artificial sequence
<220> FEATURE:
<223> OTHER INFORMATION: HapR-no linkerTobApt DNA template sequence

<400> SEQUENCE: 9
ctcgagtaat acgactcact atagggcttt aagtagcaaa taacaaaata atcattagag      60
caaaatgctc aatcaacaac tcaattggca aggatatacc cctatggacg catcttagta    120
tagcgaggtt tagctacact cgtgctgagc c                                    151

<210> SEQ ID NO 10
<211> LENGTH: 155
<212> TYPE: DNA
<213> ORGANISM: Artificial sequence
<220> FEATURE:
<223> OTHER INFORMATION: M-STobApt DNA template sequence

<400> SEQUENCE: 10
ctcgagtaat acgactcact atagaaagac gcgcatttgt tatcatcatc cctgggaaag      60
cgaggctttc cctggccact cacgagtggc cttttatatc ccccccccc ccccggctt      120 agtatagcga ggtttagcta cactcgtgct gagcc                                155

<210> SEQ ID NO 11
<211> LENGTH: 182
<212> TYPE: DNA
<213> ORGANISM: Artificial sequence
<220> FEATURE:
<223> OTHER INFORMATION: Qrr1TobApt DNA template sequence

<400> SEQUENCE: 11
ctcgagtaat acgactcact atagggtgac ccgcaagggt cacctagcca actgacgttg      60
ttagtgaata atcaatgttc acaaataaca gccaatagac tcattctatt ggctattttt    120
tttttttttt ttccccccccc ccggcttagt atagcgaggt ttagctacac tcgtgctgag    180
cc                                                                    182

<210> SEQ ID NO 12
<211> LENGTH: 157
<212> TYPE: DNA
<213> ORGANISM: Artificial sequence
<220> FEATURE:
<223> OTHER INFORMATION: MicATobApt DNA template sequence

<400> SEQUENCE: 12
ctcgagtaat acgactcact ataggggaaa gacgcgcatt tgttatcatc atccctgaat      60
tcagagatga aattttggcc actcacgagt ggccttttac acacacacac acacacgg      120 cttagtatag cgaggtttag ctacactcgt gctgagc                              157
```

```
<210> SEQ ID NO 13
<211> LENGTH: 108
<212> TYPE: DNA
<213> ORGANISM: Artificial sequence
<220> FEATURE:
<223> OTHER INFORMATION: U1TobApt DNA template sequence

<400> SEQUENCE: 13
ctcgagtaat acgactcact atagggtatc cattgcactc cggatgcctt tttttttcc      60 ccccccccgg cttagtatag cgaggtttag ctacactcgt cgtgagcc                 108

<210> SEQ ID NO 14
<211> LENGTH: 198
<212> TYPE: DNA
<213> ORGANISM: Artificial sequence
<220> FEATURE:
<223> OTHER INFORMATION: Qrr1SAApt DNA template sequence

<400> SEQUENCE: 14
ctcgagtaat acgactcact ataggtgac ccgcaagggt cacctagcca actgacgttg      60
ttagtgaata atcaatgttc acaaataaca gccaatagac tcattctatt ggctattttt    120
tttttttttt tttttttttt tttgtgtgac cgaccagaat catgcaagtg cgtaagatag    180
tcgcgggccg ggcacaca                                                  198

<210> SEQ ID NO 15
<211> LENGTH: 175
<212> TYPE: DNA
<213> ORGANISM: Artificial sequence
<220> FEATURE:
<223> OTHER INFORMATION: M-SSAApt DNA template sequence

<400> SEQUENCE: 15
ctcgagtaat acgactcact atagaaagac gcgcatttgt tatcatcatc cctgggaaag     60
cgaggctttc cctggccact cacgagtggc cttttacaca cacacacaca cacacgcatg    120
cataccgacc agaatcatgc aagtgcgtaa gatagtcgcg ggccgggatg catgc         175

<210> SEQ ID NO 16
<211> LENGTH: 178
<212> TYPE: DNA
<213> ORGANISM: Artificial sequence
<220> FEATURE:
<223> OTHER INFORMATION: MicASAApt DNA template sequence

<400> SEQUENCE: 16
ctcgagtaat acgactcact ataggggaaa gacgcgcatt tgttatcatc atccctgaat     60
tcagagatga aattttggcc actcacgagt ggccttttac acacacacac acacacgc      120 atgcataccg accagaatca tgcaagtgcg taagatagtc gcgggccggg atgcatgc     178

<210> SEQ ID NO 17
<211> LENGTH: 124
<212> TYPE: DNA
<213> ORGANISM: Artificial sequence
<220> FEATURE:
<223> OTHER INFORMATION: U1SAApt DNA template sequence

<400> SEQUENCE: 17
ctcgagtaat acgactcact atagggtatc cattgcactc cggatgcctt tttttttttt     60
tttttttttg tgtgaccgac cagaatcatg caagtgcgta agatagtcgc gggccgggca    120
caca                                                                 124
```

```
<210> SEQ ID NO 18
<211> LENGTH: 126
<212> TYPE: DNA
<213> ORGANISM: Artificial sequence
<220> FEATURE:
<223> OTHER INFORMATION: Qrr1Atail DNA template sequence

<400> SEQUENCE: 18
ctctaatacg actcactata gggtgacccg caagggtcac ctagccaact gacgttgtta      60
gtgaataatc aatgttcaca aataacagcc aatagactca ttctattggc taaaaaaaaa     120
aaaaaa                                                                126

<210> SEQ ID NO 19
<211> LENGTH: 106
<212> TYPE: DNA
<213> ORGANISM: Artificial sequence
<220> FEATURE:
<223> OTHER INFORMATION: M-SAtail DNA template sequence

<400> SEQUENCE: 19
ctcgagtaat acgactcact atagaaagac gcgcatttgt tatcatcatc cctgggaaag      60
cgaggctttc cctggccact cacgagtggc caaaaaaaaa aaaaaa                   106
```

METHOD OF IMMOBILISING RNA ONTO A SURFACE

CROSS-REFERENCE TO RELATED APPLICATIONS

This Application is a U.S. National Stage Application of PCT/GB2012/051072 filed May 14, 2012, which claims priority from Great Britain Application No. 1108041.3 May 13, 2011, both of which are incorporated by reference in their entirety.

The present invention relates to a method of generating an RNA molecule from a DNA template and immobilising the RNA molecule to a support. The invention also provides a kit for carrying out the method.

Understanding the manner in which two molecules interact lies at the heart of pharmaceutical drug development and biological research as a whole. Indeed, RNA-RNA and RNA-protein interactions are a common mechanism for many biological processes and it is believed that RNAs represent an, as yet, untapped resource in the search for novel pharmaceutical drug targets (Wahlestedt, 2006). Scientific interest in RNAs has recently been further intensified with the explosion of interest in transcriptomics, prompting the need for high-throughput analysis techniques.

Despite the current scientific interest, the study of RNA-RNA interactions to-date has been restricted by the instability of the RNA, the inability to chemically synthesize large RNAs cost effectively and the paucity of available techniques. Predominantly, RNA-RNA interactions are studied using radioactively labelled RNA methods, but it is becoming increasingly important to be able to use a wider range of techniques which can characterise the interactions in more detail. It is also essential that high-throughput techniques are developed, as the current transcriptomic tools can only identify the transcripts present and provide very limited information on the nature of their interactions with other biological molecules.

Whilst conducting research to study non-coding RNAs applicable to virulence mechanisms, the inventors discovered that these large non-coding RNAs could be successfully immobilised onto a surface plasmon resonance (SPR) sensor chip surface in an undamaged form using a novel tagging approach. This methodology has now been used to characterise the interactions of sensor-surface-immobilised large RNAs with their RNA binding partners using SPR.

The inventors then explored the commercialisation opportunities of the novel tagging approach. The tagging technology was originally conceived to create a homogeneous surface containing a single immobilised RNA. However, having demonstrated the functionality and utility, it was subsequently developed to permit the creation of multiple surface-immobilised functional RNAs in an array format. This technology has a great capacity to impact both industrial and academic research and contributes significantly to the unravelling of the complex interactions currently hidden within the transcriptome.

However, the generation of RNA arrays still proves to be challenging due to the instability of RNA and the inability to chemically synthesize large RNAs cost effectively. US 2006/0078889 discloses a method for producing RNAs using a template DNA array which is subjected to in vitro transcription. US 2004/0137439 also discloses a method of producing RNAs using a template DNA.

Sendroiu et al. (2011) discloses a method of detecting ssDNA via the microarray quantification of in situ transcribed RNA. The method comprises adsorbing ssDNA onto an ssDNA-modified gold microarray (referred to as the "generator element") through base-pairing, carrying out in situ surface transcription to obtain ssRNA, which diffuses to the adjacent detector element, wherein the resulting ssRNA is hybridised to complementary ssDNA immobilised in the detector element. Sendroiu et al. does not use a 'sandwich-based' approach (i.e. the generator and detector elements do not face each other) to use a specifically arranged DNA array to produce a maintained specific arrangement of transcribed RNAs, thereby maintaining spatial arrangement of the DNA to RNA array. Although a number of DNA spots create a number of RNA spots, all the DNA spots are the same, as are the RNA spots, as the chip is under one in vitro transcription solution. This means that only an array of a single type of RNA is possible using this method. Spatial separation of the spots to produce arrays of numerous different RNAs from different DNAs is not disclosed. Further, this document does not disclose or suggest using aptamers to immobilise RNA on a surface.

Lee et al. use a method which is fundamentally the same as that used in Sendoiu et al., meaning that it does not include a 'sandwich' format allowing for the spatial arrangement of numerous RNAs in array format. Instead, a single surface is used rather than two surfaces face-to-face, as in a 'sandwich' format.

US2010/0240544 discloses a method which is similar to Sendoiu et al. and Lee et al. in that a single surface is used such that a spot of immobilised DNA is used to transcribe an RNA aptamer containing a sequence that binds to complementary DNA immobilised in an adjacent spot. This document does not disclose a 'sandwich' format allowing the spatial arrangement of numerous RNAs in array format or use of the aptamer as a means of immobilising the RNA.

Kim et al. discloses a method of producing a DNA array. However, this does not use a 'sandwich' format to create RNA arrays of more than one RNA type. Kin et al. uses a post reaction 'print' to create DNA arrays of the same type. A 'sandwich' method cannot be employed because the tagged-DNA primers would just stick to the second surface prior to the PCR reaction. This means the second surface can only be introduced after the PCR reaction is complete and the primer is incorporated into the newly synthesised DNA strand.

The methods disclosed in the prior art documents do not allow the generation of an RNA array directly from a DNA array. Therefore, there exists a need for the development of new methods of generating and immobilising RNAs onto a support.

According to the first aspect of the present invention, there is provided a method of immobilising at least one RNA molecule onto a surface of a support comprising:
  i) providing a first support having a surface on which at least one DNA molecule is immobilised, wherein the DNA molecule encodes an RNA molecule and the encoded RNA molecule comprises a binding molecule;
  ii) providing a second support having a surface on which at least one binding partner for interacting with the binding molecule is immobilised;
  iii) arranging the first and second supports such that the surfaces displaying the immobilised molecules are in close proximity and substantially face each other, and contacting the DNA molecule immobilised on the surface of the first support with transcription reagents; and
  iv) carrying out a transcription reaction to generate the encoded RNA molecule, wherein the RNA molecule is directly immobilised onto the surface of the second support via an interaction between the binding molecule of the RNA molecule and the binding partner on the surface of the second support.

The inventors have developed a method of printing RNA arrays from DNA arrays that would allow immobilisation of full-length RNAs onto an array-format chip for high throughput probing. The RNA arrays can be generated and used immediately to avoid degradation. Accordingly, RNA molecules of large sizes, such as full length mRNA transcripts, rRNAs and tRNAs, may be generated. Unlike conventional methods of generating RNA molecules which requires an additional step of immobilising the resulting RNA molecules on a support for downstream analysis, the present invention allows the generation of RNA molecules and their immobilisation on a support to occur almost instantaneously, with little time delay and minimal handling. As will be appreciated by those skilled in the art, due to their instability, it is advantageous to handle RNA molecules as little as possible and to use them as quickly as possible to avoid contamination and degradation.

This method differs from the prior art in that it uses a 'sandwich' format. Therefore, whilst there is only a single in vitro transcription mix between the DNA surface and the surface able to bind the RNA, the sandwich arrangement means that diffusion is limited such that spatial separation of the DNA spots and RNA-binding molecules allows the generation of numerous different RNAs in an array format from a DNA array of the same format. In the methods of the prior art which use a single surface, only arrays of the same RNA are possible.

The first and second supports used in the method of the present invention can take any form. Any support having a surface suitable for immobilising DNA molecules/binding partners may be used. Preferably, the supports are solid supports which can be in the form of, for example, slides, chips, membranes, cells, microtitre wells and plates. Suitable surfaces of the supports may be, for example, made of glass, or provided with a layer of thin-film silicon (e.g. in silicon thin-film cell), gold or poly(methylethacrylate).

At least one DNA molecule can be immobilised onto the surface of the first support through a covalent or a non-covalent interaction. Covalent interactions can be achieved through coupling between an amine-including oligonucleotide and an activated carboxylate group or succinimidyl ester; coupling between a thiol-including oligonucleotide (SH-oligo) and an alkylating reagent such as an iodoacetamide or maleimide; coupling of an acrydite-oligonucleotide through a thioether; and the use of chemical linkers (e.g., without nucleotide units), such as, homopolymeric linkers (e.g., a polyethylene glycol linker) and phosphate linkages. Alternatively, the DNA molecule can be immobilized through a non-covalent interaction. Any suitable non-covalent interactions, such as electrostatic interactions, H-bondings and hydrophobic interactions, may be used. For example, the non-covalent interactions may be between a ligand that is covalently attached to the DNA molecule and a protein immobilized on the surface of the first support, e.g. between biotin and a biotin-interacting protein (e.g., streptavidin or avidin), FK506 and FK506BP, chitin and chitin binding protein, cellulose and cellulase, amylose or maltose and maltose binding protein, methotrexate and dihydrofolate reductases. The DNA molecule may also be immobilised to the surface through base pairing (i.e. H-bonding) with a complementary oligonucleotide that is covalently attached to the surface. The sequence of the complementary oligonucleotide used depends on the sequence of the DNA molecule. When a plurality of different DNA molecules are immobilised in this way, the same oligonucleotides which are complementary to a common sequence of the DNA molecules may be used, or different oligonucleotides specific for the different DNA molecules may be used.

The DNA molecule used in the present invention encodes an RNA molecule, wherein the encoded RNA molecule comprises a binding molecule. The encoded RNA molecule may be of any desirable size. For example, it may be an oligonucleotide of 10 nucleotides, or a partial or full transcript of over 10000 nucleotides. In preferred embodiments, the encoded RNA molecule is between 15 to 1500 nucleotides, for example, between 30 to 1400, 50 to 1300, 80 to 1200, 100 to 1100, 150 to 1000, 200 to 950, 300 to 900, 400 to 850 or 500 to 800 nucleotides. In addition, the encoded RNA molecule may be functional or non-functional. Functional RNA includes non-translated RNA, such as tRNA or rRNA that plays a regulatory role, and translated RNA, such as mRNA which can be translated into protein. Non-functional RNA refers to an RNA molecule which does not play any functional role. Preferably, the encoded RNA molecule is functional. In some embodiments, the RNA molecule is functional and non-coding. In other embodiments, the RNA molecule is functional and encodes a protein.

The encoded RNA molecule comprises a binding molecule. This means that a portion of the RNA molecule acts as a binding molecule to immobilise the RNA on the surface of the second support. The encoded RNA molecule will also comprise a length of RNA which does not function as a binding molecule. As explained in the paragraph above, this may be mRNA, non-translated RNA, functional non-coding RNA, tRNA, rRNA, etc.

As will be appreciated by those skilled in the art, the coding sequence of the DNA molecule is operably linked to a control sequence, which may be any control sequence that allows the transcription of the encoded RNA molecule to be carried out. As used herein, the term "operably linked" refers to a functional linkage between the control sequence and the coding sequence in order for the transcription of the encoded RNA molecule to be carried out. Preferably, the control sequence comprises a promoter.

The binding molecule of the encoded RNA molecule may be any RNA sequence that allows the encoded RNA molecule to bind to the surface of the second support. The binding molecule may be located at any position in the encoded RNA molecule. Preferably, the binding molecule is located at the 5' or 3' end of the encoded RNA molecule. More preferably, the binding molecule is located at the 3' end such that only the full length RNA molecule comprises the binding molecule, which allows the RNA molecule to be immobilised onto the surface of the second support.

In some embodiments, the binding molecule is an RNA aptamer and the corresponding binding partner immobilised on the surface of the second support is a ligand for binding to the RNA aptamer. Suitable RNA aptamers and binding partners are well known to those skilled in the art. For example, tobramycin and tobramycin-binding aptamer, or streptavidin and streptavidin binding aptamer can be used in the method of the present application. Alternatively, the binding partner immobilised on the surface of the second support may be an oligonucleotide (RNA or DNA) that is complementary to the binding molecule of the RNA molecule. When a plurality of different RNA molecules are generated, the same oligonucleotides which are complementary to a common sequence of the encoded RNA molecules (i.e. the binding molecules of the different RNA sequences are the same) may be used, or different oligonucleotides specific for the different RNA molecules (i.e. the binding molecules of the different RNA sequences are different) may be used.

In some embodiments, a plurality of DNA molecules are immobilised on the surface of the first support. In particular, any number of DNA molecules can be immobilised. For example, 2, 5, 10, 50, 100 or more DNA molecules may be immobilised. The number of the immobilised DNA molecules may be as high as 1000, 10000, 100000, 1000000 or higher. In general, the plurality of DNA molecules are sufficiently spaced from one another such that the RNA molecules resulting from the transcription of two adjacent DNA molecules do not mix. In some embodiments, the plurality of DNA molecules are immobilised onto the surface of the first and second supports in an array format.

In addition, the coding sequences of the plurality of DNA molecules may be homogeneous such that the encoded RNA molecules have the same sequences, or heterogeneous such that the encoded RNA molecules have different sequences. In the latter embodiment, the heterogeneous RNA molecules may comprise the same or different binding molecules. In some embodiments, the plurality of DNA molecules encode RNA molecules having different sequences, wherein the binding molecules of the RNA molecules are the same. This arrangement allows the use of a universal binding partner for immobilising different RNA molecules. Therefore, the same second support having the universal binding partners immobilised thereon can be used for immobilising RNA molecules encoded by different DNA molecules. In other embodiments, the plurality of DNA molecules encode RNA molecules having different sequences, wherein the binding molecules of the RNA molecules are different. A plurality of binding molecules may be present. For example, some RNA molecules may comprise a first binding molecule and other RNA molecules may comprise a second different binding molecule.

Similarly, a plurality of binding partners for interacting with the binding molecules may be immobilised on the surface of the second support. The plurality of binding partners may be the same or different, depending on the identities of the binding molecules of the encoded RNA molecules. For example, where the plurality of binding partners are different, some of the binding partners may be a first binding partner and others may be a second different binding partner, i.e. the binding partners are selected from two different binding partners.

In some embodiments, the control sequence, e.g. the promoter sequence, of the immobilised DNA molecule is located towards the proximal end (i.e. close to the surface of the first support). In such embodiments, the DNA molecule may comprise a spacer between the proximal end of the DNA molecule and the promoter. In other embodiments, the promoter sequence may be located towards the distal end (i.e. away from the surface of the first support), and the coding sequence of the DNA molecule may be located towards the proximal end. In such embodiments, the DNA molecule may comprise a spacer between the proximal end and the coding sequence.

In preferred embodiments, the DNA molecule is orientated such that the binding molecule of the encoded RNA molecule is located towards the distal end away from the surface of the first support. This arrangement facilitates the interaction between the binding molecule of the encoded RNA molecule and the binding partner immobilised on the surface of the second support.

In some embodiments, the DNA molecule may comprise a spacer between the sequence encoding the binding molecule and the remaining coding sequence.

Suitable spacers are well known to those skilled in the art, for example, they may be between 1 and 200 nucleotides in length. In some embodiments, they may be between 2 and 150 nucleotides in length, between 5 and 100 nucleotides, between 6 and 95 nucleotides, between 10 and 90, or between 15 and 85 nucleotides.

Any promoter sequence specific for an RNA polymerase may be used in the present invention. The RNA polymerase can be prokaryotic, eukaryotic, or archeal. For example, the RNA polymerase can be a prokaryotic bacteriophage RNA polymerase such as the T7, T3, SP6, and N4 RNA polymerases. Hence, exemplary promoter sequences include, but are not limited to, T7, T3, Sp6 and N4 RNA polymerase promoter sequences. Other promoter sequences, such as SP01 promoters, can be used in conjunction with sigma factors from the *Bacillus subtilis* phage SP01 to target RNA polymerase to the SP01 promoters. Preferably, T7 RNA polymerase and the corresponding promoter sequence are used in the present invention.

The DNA molecule used in the present invention may be single stranded or double stranded or partially double stranded. For example, the DNA molecule may be a mostly single stranded molecule having a double stranded portion at the promoter region. Depending on the RNA polymerase to be used for the transcription reaction, the promoter region may be single stranded or double stranded. For example, bacteriophage N4 RNA polymerase uses a single stranded promoter sequence, and T7 RNA polymerase uses a double stranded promoter sequence. When a single stranded DNA molecule is used, a double stranded promoter region is generated for use with an RNA polymerase that recognises a double stranded promoter region.

The first and second supports may be arranged in any alignment so long as the surfaces of the supports displaying the immobilised molecules are in close proximity and substantially face each other. By "close proximity" and "substantially face each other", it is meant that the DNA molecule immobilised on the surface of the first support are in the vicinity of the binding partner immobilised on the surface of the second support, such that the binding molecule of the RNA molecule generated from the transcription reaction interact with the immobilised binding partner with limited diffusion. Accordingly, the RNA molecules synthesised on the DNA-immobilised first support would substantially immediately bind to the adjacent binding partner-immobilised second support through an interaction between the binding molecule of the RNA molecule and the binding partner. The surface of the second support should be present whilst the transcription reaction is taking place so that the generated RNA molecule can bind to the binding partner straightaway, thereby helping to limit diffusion.

In some embodiments, a membrane may be positioned between the first and second surfaces so as to minimise diffusion. The membrane is positioned so that it extends from the first surface to the second surface. This means that RNA molecules produced at the first surface are free to diffuse towards and bind to the binding partner attached to the second surface. However, the membrane limits diffusion along the surfaces by minimising the movement of RNA molecules along the surface and away from the opposing binding partner.

The membrane may be positioned so that it limits diffusion in a particular area. For example, the membrane may substantially encompass or surround an area on the first surface so that the RNA molecules produced in that area are restricted from diffusing out of that area by the membrane and instead diffuse towards a corresponding area encompassed by the membrane on the second surface. In some embodiments, there may be a plurality of membranes positioned between the first and second surface.

The membrane has pores allowing the RNA to be transcribed but minimising diffusion and focusing the RNA to the binding molecule opposite the DNA. For example, the membrane may be soaked in in vitro transcription mix. Suitable membranes include whatman paper, whatman membrane filters, Millipore Durapore membrane filters, etc.

In some embodiments, the positions at which the DNA molecules are immobilised on the surface of the first support substantially correspond to the positions at which the binding partners are immobilised on the surface of the second support. In these embodiments, the first and second supports are arranged such that the corresponding positions on the first and second support are substantially aligned. In some embodiments, the entire surface of the second support, or at least a substantial portion thereof, may have binding partners immobilised thereon. In such embodiments, the first and second supports may be arranged in any alignment, and only the positions on the surface of the second support, which correspond to the positions where DNA molecules are immobilised on the surface of the first support, will have RNA molecules immobilised thereon. In this way, the same binding partner-immobilised second support can be used for immobilising RNA molecules regardless of the arrangement of the DNA molecules immobilised on the surface of the first support. In any event, following transcription, the surface of the second support will represent an RNA replica of the DNA-immobilised surface of the first support.

In preferred embodiments, the surfaces of the first and second supports are not in direct contact (although still in close proximity) so as to avoid damage to the surfaces and/or to limit physical displacement of the synthesised RNA molecules by the surfaces of the first and second supports. In some embodiments, the surfaces of the first and second supports are separated by a gap of at least about 1 nm. In certain embodiments, the surfaces of the first and second supports are separated by a gap of about 10-200 μm, or about 20-180 μm, or about 40-160 μm, or about 50-150 μm, or about 60-130 μm, or about 80-120 μm. Any suitable spacing element may be used to separate the two surfaces. Essentially, the spacing element is sandwiched between the two supports and the immobilised molecules extend into the gap formed between the surfaces of the supports. As will be appreciated by those skilled in the art, the spacing element may be provided separately to the supports, e.g. a piece of parafilm or a glass coverslip. Alternatively, the spacing element may be formed as an integral part of one or both of the supports, e.g. a projection on the surface of one or both of the supports.

Contacting the DNA molecule immobilised on the surface of the first support with transcription reagents can take place before or after the first and second supports have been arranged as discussed above. For example, the transcription reagents can be placed on the surface of the first support to contact the DNA molecule immobilised thereon, and then the first and second supports are arranged as described above. Alternatively, the first and second supports can be arranged first, and then the transcription reagents are applied to contact the immobilised DNA molecule. In any event, during the transcription reaction, the surfaces displaying the immobilised molecules are in close proximity and substantially face each other.

As will be appreciated by those skilled in the art, the transcription reagents contain components necessary for carrying out the transcription reaction. For example, an RNA polymerase, NaCl, $Mg_2Cl_2$, Tris-HCl, rNTPs, DTT and an RNase inhibitor may be used. Some labelled rNTPs may be included to produce labelled RNA molecules to facilitate subsequent detection. Depending on the intended detection method, the labels can be, but are not limited to, fluorescent dyes, such as fluorescein and the cyanine dyes (Cy3, Cy5, Alexa 542, and Bodipy 630/650), radiolabels, such as $^{32}P$, $^{33}P$, $^{35}S$ and $^{3}H$, colorimetric or chemiluminescent labels.

Once the transcription reaction is carried out, the encoded RNA molecule comprising a binding molecule is obtained. Since the DNA molecule immobilised on the surface of the first support is in close proximity to the binding partner immobilised on the surface of the second support, the RNA molecule generated, particularly its binding molecule, is so close to the binding partner that the RNA molecule becomes directly immobilised onto the surface of the second support. By "directly immobilised", it is meant that the immobilisation of the RNA molecule occurs almost instantaneously as the RNA molecule, particularly the binding molecule, is generated. In particular, the RNA molecule is immobilised to the surface of the second support with limited diffusion. This means that the RNA molecule generated at a particular position on the DNA-immobilised surface of the first support is immobilised to the corresponding position on the binding partner-immobilised surface of the second support, without diffusing to an adjacent position on the DNA-immobilised surface of the first support or other positions on the binding partner-immobilised surface of the second support which are not in the immediate vicinity of the position where the RNA molecule is generated.

The RNA molecules produced by the method of the present invention find use in a variety of different applications. For example, an RNA array representing an entire transcriptome may be generated, which can then be used for screening the transcriptome for interactions with potential ligands. In applications for targeting RNA viruses and drug screening, the potential ligands may be agonists or antagonists. The potential ligands may be labelled (e.g. radiolabelled or fluorescently labelled) to allow the detection of interactions between the RNA molecules and the potential ligands. Alternatively, the interactions may be monitored using SPR.

In addition, the RNA molecules produced by the method of the present invention may be translated to produce the encoded protein molecules. As will be appreciated by those skilled in the art, in order for the resulting RNA molecules to be used in this application, the RNA molecules need to include the necessary control sequences for translation to be carried out. For example, the RNA molecules may include a translation initiation site/ribosome binding site. In some embodiments, the RNA molecule immobilised on the second support encodes for a protein comprising a tag. In such embodiments, the encoded protein molecule may be immobilised onto a third support following translation. In particular, a third support having a surface on which a corresponding binding partner for the tag is immobilised is provided. The second and third supports are then arranged such that the surfaces displaying the immobilised molecules are in close proximity and substantially face each other, and the RNA molecule immobilised on the surface of the second support is contacted with translation reagents to allow translation to occur. Similar to the generation and immobilisation of the RNA molecule onto the second support, the encoded protein molecule comprising the tag is directly immobilised onto the surface of the third support via the interaction between the tag of the protein molecule and the corresponding binding partner on the surface of the third support following translation. Suitable tags and binding partners are well known to those skilled in the art. They include, but are not limited to, polyhistidine residues (e.g. 6-His) as a tag and nickel (e.g. nickel-nitriloacetic acid) as the binding partner. Accordingly, in addition to the generation of an RNA-print of the DNA molecules, the present invention may also be used to make a protein-print of the DNA molecules using the RNA-print.

When the user has finished with using the RNA molecules, he may remove the RNA molecules from the surface of the second support and reuse the support for immobilising a new set of RNA molecules. Similarly, the DNA-immobilised surface of the first support may be reused. For example, if a chip of DNA templates is used, the chip can be washed free of reagents. The washed chip can either be immediately reused for additional rounds of transcription or stored, e.g. in an archival process. A stored chip can be dehydrated or frozen, or coated with a cryoprotectant such as a glycerol solution, and frozen. A stored chip can be retrieved, washed and applied with fresh transcription reagents.

According to a second aspect of the present invention, there is provided a kit for carrying out the method according to the first aspect, the kit comprising: i) a first support having a surface comprising at least one DNA molecule immobilised thereon, wherein the at least one DNA molecule encodes an RNA molecule and the encoded RNA molecule comprises a binding molecule; ii) a second support having a surface for immobilising the RNA molecule encoded by the at least one DNA thereon; and iii) transcription reagents. The surface of the second support has at least one binding partner immobilised thereon. The binding partner is suitable for interacting with the binding molecule of the encoded RNA molecule.

In use, the surfaces of the first and second support displaying the immobilised molecules are in close proximity and substantially face each other when the transcription reaction is being carried out.

The kit of the present invention allows RNA molecules (e.g. RNA arrays) to be generated and used immediately to avoid degradation. The kit can be used repeatedly for generating and immobilising RNA molecules to the surface of the second support (as discussed above).

In certain embodiments, the kit further comprises means for securing the first and second supports such that the surfaces displaying the immobilised molecules are in close proximity and substantially face each other. Suitable means for securing the first and second supports are well known to those skilled in the art. For example, clamps may be used for securing the alignments of the first and second supports. Alternatively, the first and second supports may comprise connecting means to secure the supports. Suitable connecting means are well known to those skilled in the art. For example, one of the supports may comprise a groove and the other may comprise a corresponding projection. The groove and projection allows the correct alignment of the supports.

In some embodiments, the kit further comprises means for preventing the surfaces of the first and second supports from coming into direct contact. As mentioned above, the surfaces of the first and second supports may be separated by a gap of at least about 1 nm. In some embodiments, the surfaces of the first and second supports may be separated by a gap of about 10-200 µm, or about 20-180 µm, or about 40-160 µm, or about 50-150 µm, or about 60-130 µm, or about 80-120 µm. In particular, the surfaces may be separated by a spacing element.

The terms "first support", "second support", "binding molecule", "binding partner", "transcription reagents" and "spacing element" used in the second aspect of the invention are as defined in the first aspect of the invention.

The invention will now be described in detail by way of examples only with reference to the following figures:

FIG. 1. 'Sandwich print' set-up arrangement. A schematic diagram is shown illustrating the sandwich arrangement of the DNA-template slide, with immobilised DNA template encoding the RNA of interest, +/− linker, with a specific tag (e.g. tobramycin aptamer (TobApt), streptavadin aptamer (SAApt), poly-A sequence (Atail)). The tag provides a means of enabling the subsequently synthesised RNA to bind to surface-immobilised binding-partner molecules (e.g. tobramycin, streptavadin, poly-dT) immobilised on the RNA-binding slide facing the DNA-template slide. The slides are sandwiched such that the DNA and RNA-binding molecules are aligned, although in some situations the RNA-binding slide can be completely coated in the RNA-binding molecule, removing the need for alignment. In all cases, the DNA-template and RNA-binding slides both face inwards, with the in vitro transcription mix in between. A small piece of parafilm at the ends of the slides is used as a spacer to prevent the slide surfaces from coming into direct contact.

Figure 2:
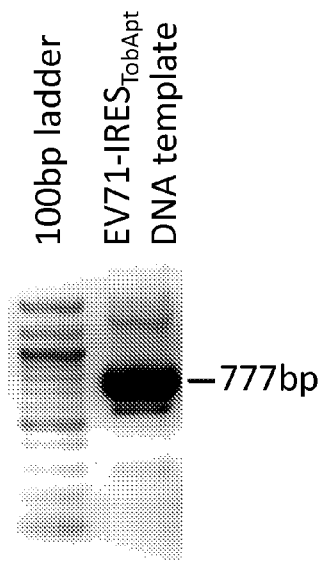

FIG. 2. Example gel showing that biotin-tagged DNA template is pure. Shown is a photograph of an 1.2% agarose gel following electrophoresis of PCR synthesised EV71-IRES$_{TobApt}$ DNA. The DNA was stained with ethidium bromide and visualised under UV. The successful synthesis of the Biotin-DNA template at high purity is seen by the band on the gel of the correct size.

Figure 3:
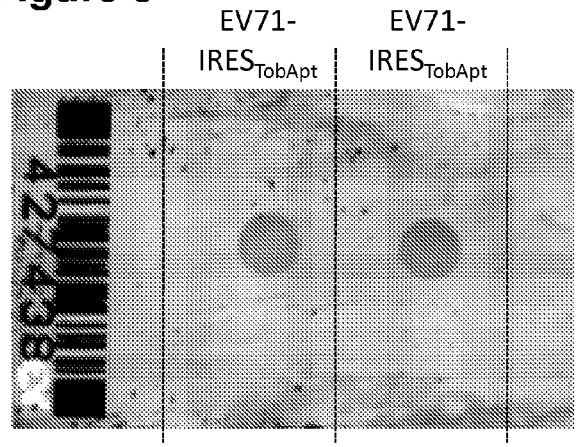

FIG. 3. EV71-IRES$_{TobApt}$ RNA is successfully 'sandwich printed' onto a tobramycin RNA-binding slide. Shown is a photograph of a tobramycin slide following 'sandwich printing' of the RNA molecule, EV71-IRES$_{TobApt}$, synthesised from transcription of Biotin-EV71-IRES$_{TobApt}$. The RNA molecules bound to the tobramycin were stained with SYBR gold and visualized under UV.

Figure 4:
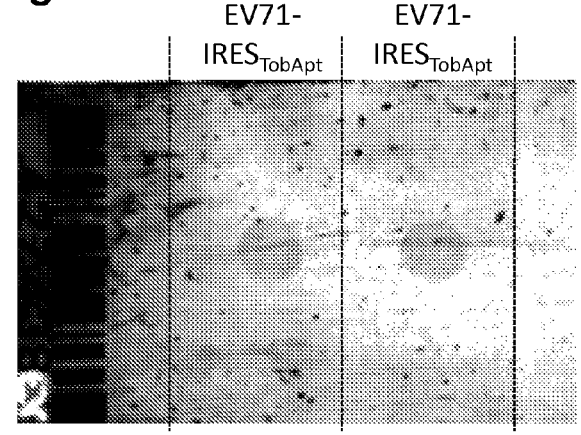

FIG. 4. 'Sandwich printed' EV71-IRES$_{TobApt}$ RNA binds stably to the tobramycin RNA-binding slide. Shown is a photograph of the tobramycin slide from FIG. 3 following 3 washes with PBS buffer. EV71-IRES$_{TobApt}$ RNA is stably bound to tobramycin as it is still detected following 3 washes with PBS.

Figure 5:
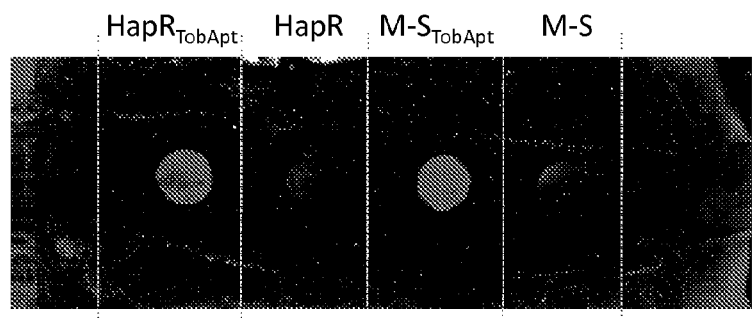

FIG. 5. 'Sandwich printed' tobramycin apatmer (TobApt)-tagged RNAs are bound specifically to the tobramycin RNA-binding slide. RNAs HapR+/−TobApt and M-S+/−TobApt were 'sandwich printed' from their corresponding DNA template, in a four spot array format, on the DNA template slide, onto the tobramycin RNA-binding slide opposite. Cy$^5$-labelled UTP was included in the in vitro transcription mix resulting in the RNAs produced being Cy$^5$-labelled. Shown is the tobramycin RNA-binding slide, visualised at 639 nm for Cy$^5$. Only the HapR$_{TobApt}$ and M-S$_{TobApt}$ bound to the tobramycin, as seen by the spots. The non-TobApt-RNAs failed to bind.

Figure 6:
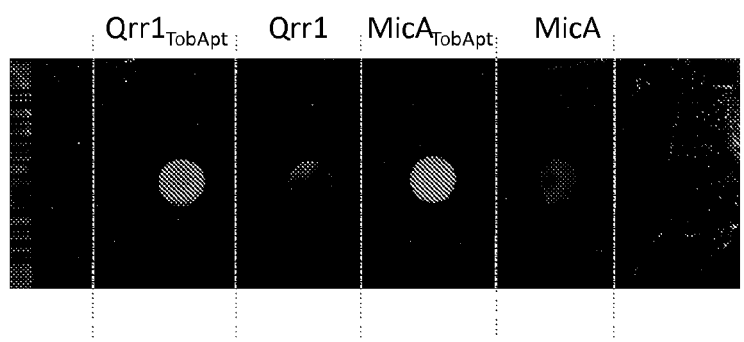

FIG. 6. As for FIG. 5, except the RNAs used were Qrr1+/−TobApt and MicA+/−TobApt. Cy$^3$-labelled UTP was included in the in vitro transcription mix resulting in the RNAs produced being Cy$^3$-labelled. Shown is the tobramycin RNA-binding slide, visualised at 532 nm for Cy$^3$. Only the Qrr1$_{TobApt}$ and MicA$_{TobApt}$ bound to the tobramycin, as seen by the spots. The non-TobApt-RNAs failed to bind.

Figure 7:
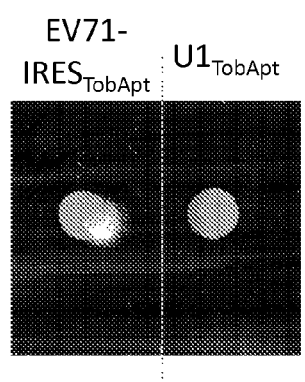

FIG. 7. TobApt-RNAs of a range of sizes can be immobilised using the 'sandwich print' method. Shown is a tobramycin RNA-binding slide following 'sandwich printing' with EV71-IRES$_{TobApt}$ and U1$_{TobApt}$ RNAs of 623 and 25 nucleotides respectively (with linkers of 83 and 20 nucleotides respectively and TobApt of 40 nucleotides). Cy$^3$ UTP was incorporated in the in vitro transcription and the slide visualised at 532 nm showing the immobilised RNAs as spots.

Figure 8:
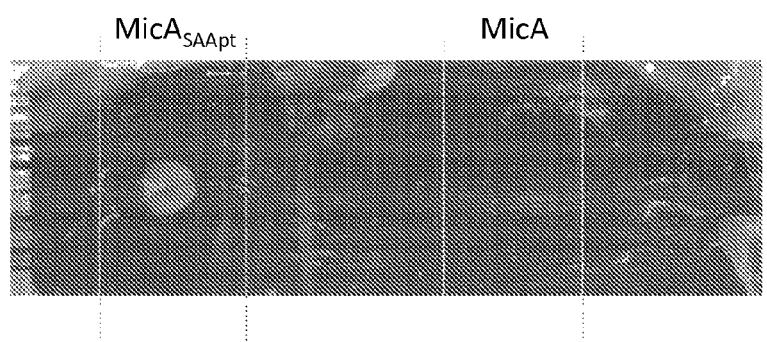

FIG. 8. 'Sandwich printed' streptavidin apatmer (SAApt)-tagged RNAs are bound specifically to the streptavidin RNA-binding slide. RNA MicA+/−SAApt was 'sandwich printed' from its corresponding DNA template on the DNA-template slide onto the streptavidin RNA-binding slide opposite. Cy$^3$-labelled UTP was included in the in vitro transcription mix, between the slides, resulting in the RNA produced being Cy$^3$-labelled. Shown is the streptavidin RNA-binding slide, visualised at 532 nm for Cy$^3$. Only the MicA$_{SAApt}$ bound to the streptavidin RNA-binding slide, as seen by the spot. The non-SAApt-RNA (MicA) failed to bind.

Figure 9:
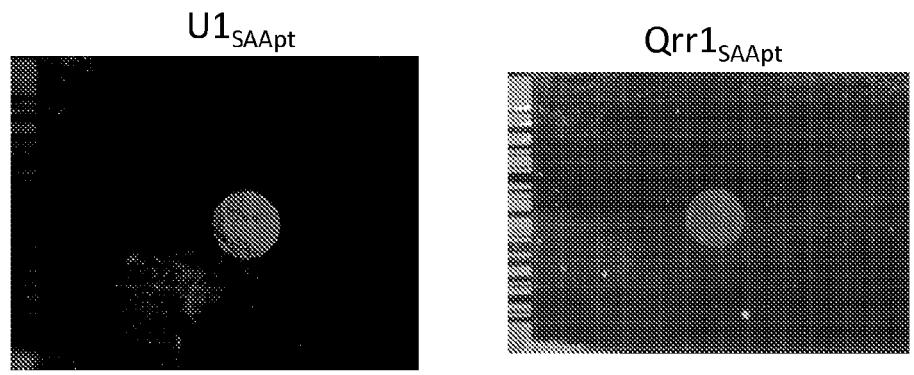

FIG. 9. Different SAApt-RNAs can be immobilised using the 'sandwich print' method. Shown is a streptavidin RNA-binding slide following 'sandwich printing' with U1$_{SAApt}$ and Qrr1$_{SAApt}$ RNAs of 25 and 99 nucleotides respectively (both with linkers of 26 nucleotides and SAApt of 44 nucleotides). Cy$^5$ UTP was incorporated in the in vitro transcription for Qrr1$_{SAApt}$ and the slide visualised at 639 nm whereas Cy$^3$ UTP was incorporated in the in vitro transcription for U1$_{SAApt}$ and the slide visualised at 532 nm. The 'sandwich printed' U1$_{SAApt}$ and Qrr1$_{SAApt}$ are seen as spots.

Figure 10:
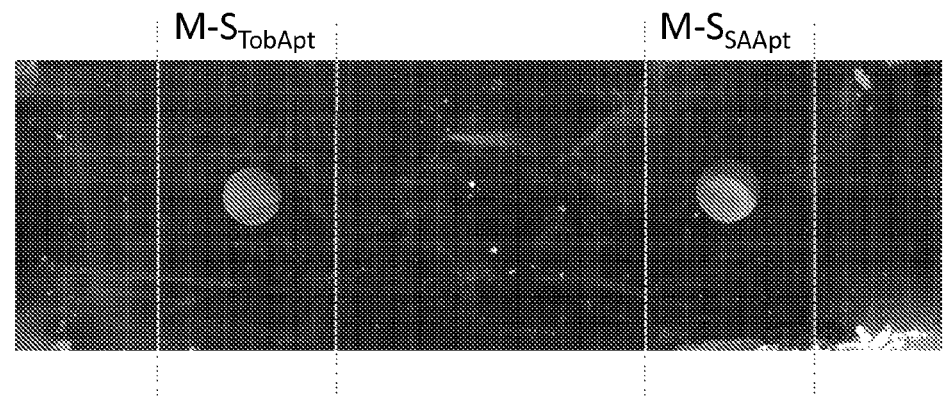

FIG. 10. RNA's can be 'sandwich printed' on the same array slide via different RNA tags. RNAs M-S$_{TobApt}$ and M-S$_{SAApt}$ were 'sandwich printed' from their corresponding DNA template, in a two spot array format on the DNA template slide, onto an RNA-binding slide opposite spotted with the corresponding RNA binding molecules of tobramycin and streptavidin. Cy$^3$-labelled UTP was included in the in vitro transcription mix resulting in the RNAs produced being Cy$^3$-labelled. Shown is the tobramycin and streptavidin spotted RNA-binding slide, visualised at 532 nm for Cy$^3$. Both M-S$_{TobApt}$ and M-S$_{SAApt}$ are seen by the spots.

Figure 11:
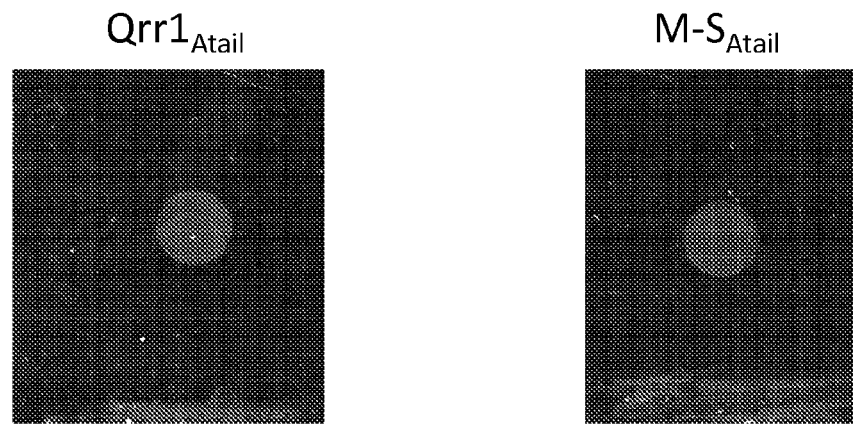

FIG. 11. RNAs transcribed using the 'sandwich print' method and incorporating a 15mer polyA-tail (Atail) can be immobilised to a poly-dT RNA-binding slide. Shown is a poly-dT RNA-binding slide following 'sandwich printing' of Qrr1$_{Atail}$ and M-S$_{Atail}$ RNAs of 91 and 68 nucleotides respectively (plus polyA-tail of 15 nucleotides respectively). Cy$^5$ UTP was incorporated in the in vitro transcription reaction and the slide visualised at 639 nm. The bound RNA is seen as spots.

MATERIALS AND METHODS

Preparation of DNA Templates

EV71-IRES$_{TobApt}$ was PCR-amplified from pCRII IRES EV71 tob (Nicolas Locker, University of Surrey) using a biotinylated primer corresponding to the T7 promoter sequence (5' biotin-ctc gag taa tac gac tca cta tag g 3' (SEQ ID NO: 1), the T7 promoter sequence is in bold) and a primer complementary to the 3' end of the EV71-IRES$_{TobApt}$ sequence (5' agagagGGCTCAGCACGAGTGTAG 3' (SEQ ID NO: 2), the region complementary to the 3' end of the tobramycin aptamer sequence is in capitals). The DNA was cleaned up using the Nucleospin Extract II Kit (Macherey-Nagel, Düren, Germany).

The EV71-IRES$_{TobApt}$ DNA template sequence is shown below:

(SEQ ID NO: 3)
Biotin-ctc gag taa tac gac tca cta taG GGA GAC GAT

CAA TAG CAG GTG TGG CAC ACC AGT CAT ACC TTG ATC

AAG CAC TTC TGT TTC CCC GGA CTG AGT ATC AAT AGG

CTG CTC GCG CGG CTG AAG GAG AAA ACG TTC GTT ACC

CGA CCA ACT ACT TCG AGA AGC TTA GTA CCA CCA TGA

ACG AGG CAG GGT GTT TCG CTC AGC ACA ACC CCA GTG

TAG ATC AGG CTG ATG AGT CAC TGC AAC CCC AT GGG

CGA CCA TGG CAG TGG CTG CGT TGG CGG CCT GCC CAT

GGA GAA ATC CAT GGG ACG CTC TAA TTC TGA CAT GGT

GTG AAG AGC CTA TTG AGC TAG CTG GTA GTC CTC CGG

CCC CTG AAT GCG GCT AAT CCT AAC TGC GGA GCA CAT

GCT CAC AAA CCA GTG GGT GGT GTG TCG TAA CGG GCA

ACT CTG CAA CGG AAC CGA CTA CTT TGG GTG TCC CGT

GTT TCC TTT TAT TCC TAT ATT GGC TGC TTA TGG TGA

CAA TCA AAA AGT TGT TAC CAT ATA GCT ATT GGA TTG

GCC ATC CGG TGT GCA ACA GGG CAA TTG TTT ACC TAT

TTA TTG GTT TTG TAC CAT TAT CAC TGA AGT CTG TGA

TCA CTC TCA AAT TCA TTT TGA CCC TCA ACA CAA TCA

AAC *atg agc acg aat cct aaa cct caa aga aaa acc*

*aaa cgt aac acc aac cgt cgc cca caa acc tcg act*

*ctt cta gac tct ct*g gct tag tat agc gag gtt tag cta cac tcg tgc tga gcc ctc tct (T7 promoter—bold; transcriptional start site—bold and underlined; EV71-IRES—capitals (623 nt); Linker—italics (83 nt); Tobramycin-binding aptamer (TobApt)—underlined (40 nt))

All other DNA templates were generated by the extension of overlapping primers (Gao et al., (2003)). This was followed by PCR amplification using a biotinylated or thiolated primers corresponding to the T7 promoter sequence (5' biotin/thiol-ctc gag taa tac gac tca cta tag g 3' (SEQ ID NO: 1), the T7 promoter sequence is in bold) and a primer corresponding to the 3' end of the required DNA sequence. This generated biotin/thiol-tagged DNA template for subsequent immobilisation to DNA-template slides. The DNA was cleaned up using the Nucleospin Extract II Kit (Macherey-Nagel, Düren, Germany).

Below is a list of the sequences of the DNA templates prepared in this manner:

1. HapR (SEQ ID NO: 4)
Biotin-ctc gag taa tac gac tca cta taG GGC TTT AAG

TAG CAA ATA ACA AAA TAA TCA TTA GAG CAA AAT GCT

CAA TCA ACA ACT CAA TTG GCA AGG ATA TAC CCC TAT

GGA CGC AT (T7 promoter—bold; Transcriptional start site—capitals and underlined; HapR—capitals (90 nt)).

2. MicA$_{stab}$ (SEQ ID NO: 5)
Biotin-ctc gag taa tac gac tca cta ta<u>G</u> AAA GAC GCG CAT TTG TTA TCA TCA TCC CTG GGA AAG CGA GGC TTT CCC TGG CCA CTC ACG AGT GGC CTT TT (T7 promoter—bold; Transcriptional start site—capitals and underlined; MicA$_{stab}$—capitals (71 nt)).

3. Qrr1

(SEQ ID NO: 6)
Biotin-ctc gag ta ata cga ctc act ata <u>GGG</u> TGA CCC GCA AGG GTC ACC TAG CCA ACT GAC GTT GTT AGT GAA TAA TCA ATG TTC ACA AAT AAC AGC CAA TAG ACT CAT TCT ATT GGC TAT TTT TTT (T7 promoter—bold; Transcriptional start site—bold and underlined; Qrr1—capitals (99 nt)).

4. MicA (SEQ ID NO: 7)
Biotin-ctc gag taa tac gac tca cta ta <u>GGG</u> GAA AGA CGC GCA TTT GTT ATC ATC ATC CCT GAA TTC AGA GAT GAA ATT TTG GCC ACT CAC GAG TGG CCT TTT (T7 promoter—bold; Transcriptional start site—capital and underlined; MicA—capitals (75 nt)).

5. HapR$_{TobApt}$ (SEQ ID NO: 8)
Biotin-ctc gag taa tac gac tca cta ta<u>G</u> GGC TTT AAG TAG CAA ATA ACA AAA TAA TCA TTA GAG CAA AAT GCT CAA TCA ACA ACT CAA TTG GCA AGG ATA TAC CCC TAT GGA CGC AT *a aaa aaa aaa aaa aaa aaa* <u>ctt agt ata gcg agg ttt agc tac act cgt gct gag cc</u>

(T7 promoter—bold; Transcriptional start site—capitals and underlined; HapR—capitals (90 nt); Linker—italics (19 nt); Tobramycin aptamer—lower case, underlined (38 nt)).

6. HapR-no linker$_{TobApt}$ (SEQ ID NO: 9)
Biotin-ctc gag taa tac gac tca cta ta<u>G</u> GGC TTT AAG TAG CAA ATA ACA AAA TAA TCA TTA GAG CAA AAT GCT CAA TCA ACA ACT CAA TTG GCA AGG ATA TAC CCC TAT GGA CGC AT <u>ctt agt ata gcg agg ttt agc tac act cgt gct gag cc</u>

(T7 promoter—bold; Transcriptional start site—capitals and underlined; HapR—capitals (90 nt); Tobramycin aptamer—lower case, underlined (38 nt))

7. M-S$_{TobApt}$ (SEQ ID NO: 10)

Biotin-ctc gag taa tac gac tca cta ta<u>G</u> AAA GAC GCG CAT TTG TTA TCA TCA TCC CTG GGA AAG CGA GGC TTT CCC TGG CCA CTC ACG AGT GGC CTT TT *ata tcc ccc ccc ccc ccc cc* <u>ggc tta gta tag cga ggt tta gct aca ctc gtg ctg agc c</u>

(T7 promoter—bold; Transcriptional start site—capital and underlined; M-S—capitals (71 nt); Linker—italics (20 nt); Tobramycin binding aptamer$_{(TobApt)}$—underlined (40 nt)).

8. Qrr1$_{TobApt}$ (SEQ ID NO: 11)

Biotin-ctc gag ta ata cga ctc act ata <u>GGG</u> TGA CCC GCA AGG GTC ACC TAG CCA ACT GAC GTT GTT AGT GAA TAA TCA ATG TTC ACA AAT AAC AGC CAA TAG ACT CAT TCT ATT GGC TAT TTT TTT *ttt ttt ttt tcc ccc ccc cc* <u>g gct tag tat agc gag gtt tag cta cac tcg tgc tga gcc</u>

(T7 promoter—bold; Transcriptional start site—capitals and underlined; Qrr1—capitals (99 nt); Linker—italics (20 nt); Tobramycin binding aptamer$_{(TobApt)}$—underlined (40 nt)).

9. MicA$_{TobApt}$ (SEQ ID NO: 12)

Biotin-ctc gag taa tac gac tca cta ta <u>GGG</u> GAA AGA CGC GCA TTT GTT ATC ATC ATC CCT GAA TTC AGA GAT GAA ATT TTG GCC ACT CAC GAG TGG CCT TTT *aca cac aca cac aca cac ac* <u>ggc tta gta tag cga ggt tta gct aca ctc gtg ctg agc c</u>

(T7 promoter—bold; Transcriptional start site—capitals and underlined; MicA—capitals (75 nt); Linker—italics (20 nt); Tobramycin binding aptamer$_{(TobApt)}$—underlined (40 nt)).

10. U1$_{TobApt}$ (SEQ ID NO: 13)

Biotin-ctc gag taa tac gac tca cta ta<u>G GG</u> TAT CCA TTG CAC TCC GGA TGC C *ttt ttt ttt tcc ccc ccc cc* <u>g gct tag tat agc gag gtt tag cta cac tcg tcg tga gcc</u>

(T7 promoter—bold; Transcriptional start site—capitals and underlined; U1—capitals (25 nt); Linker—italics (20 nt); Tobramycin binding aptamer$_{(TobApt)}$—underlined (40 nt)).

11. Qrr1$_{SAApt}$ (SEQ ID NO: 14)

Biotin-ctc gag ta ata cga ctc act ata <u>GGG</u> TGA CCC GCA AGG GTC ACC TAG CCA ACT GAC GTT GTT AGT GAA TAA TCA ATG TTC ACA AAT AAC AGC CAA TAG ACT CAT TCT ATT GGC TAT TTT TTT *ttt ttt ttt ttt ttt gtg tg* <u>acc gac cag aat cat gca agt gcg taa gat agt cgc ggg ccg gg cac aca</u>

(T7 promoter—bold; Transcriptional start site—capitals and underlined; Qrr1—capitals (99 nt); Linker—italics (26 nt); Streptavidin binding aptamer$_{(SAApt)}$—underlined (44 nt); Linker 2—italics underlined (6 nt)).

12. M-S$_{SAApt}$ (SEQ ID NO: 15)

Biotin-ctc gag taa tac gac tca cta ta<u>G</u> AAA GAC GCG CAT TTG TTA TCA

TCA TCC CTG GGA AAG CGA GGC TTT CCC TGG CCA CTC ACG

AGT GGC CTT TT *aca cac aca cac aca cac acg cat gca t* <u>acc gac cag aat cat</u>

<u>gca agt gcg taa gat agt cgc ggg ccg gg</u> *<u>atg cat gc</u>*

(T7 promoter—bold; Transcriptional start site—capital and underlined; MicA$_{stab}$—capitals (72 nt); Linker—italics (28 nt); Streptavidin binding aptamer$_{(SAApt)}$—underlined (44 nt); Linker 2—italics underlined (8nt)).

13. MicA$_{SAApt}$ (SEQ ID NO: 16)

Biotin-ctc gag taa tac gac tca cta ta <u>GGG</u> GAA AGA CGC GCA TTT GTT

ATC ATC ATC CCT GAA TTC AGA GAT GAA ATT TTG GCC ACT CAC

GAG TGG CCT TTT *aca cac aca cac aca cac acg cat gca t* <u>acc gac cag aat cat</u>

<u>gca agt gcg taa gat agt cgc ggg ccg gg</u> *<u>atg cat gc</u>*

(T7 promoter—bold; Transcriptional start site—capitals and underlined; MicA—capitals (75 nt); Linker—italics (28 nt); Streptavidin binding aptamer$_{(SAApt)}$—underlined (44 nt); Linker 2—italics underlined (8 nt)).

14. U1$_{SAApt}$ (SEQ ID NO: 17)

Biotin-ctc gag taa tac gac tca cta ta<u>G GGT</u> ATC CAT TGC ACT CCG GAT GCC *ttt ttt ttt ttt ttt ttt ttt gtg tg* <u>acc gac cag aat cat gca agt gcg taa</u>

<u>gat agt cgc ggg ccg gg</u> *cac aca*

(T7 promoter—bold; Transcriptional start site—capitals and underlined; U1—capitals (25 nt); Linker—italics (26 nt); Streptavidin binding aptamer$_{(SAApt)}$—underlined (44 nt); Linker 2—italics underlined (6 nt)).

15. Qrr1$_{Atail}$ (SEQ ID NO: 18)

Biotin-ctc ta ata cga ctc act ata <u>GGG</u> TGA CCC GCA AGG GTC ACC TAG

CCA ACT GAC GTT GTT AGT GAA TAA TCA ATG TTC ACA AAT

AAC AGC CAA TAG ACT CAT TCT ATT GGC T *aaa aaa aaa aaa aaa*

(T7 promoter—bold; Transcriptional start site—capitals and underlined; Qrr1—capitals (91 nt); polyA$_{(A\ tail)}$—italics (15 nt)).

16. M-S$_{Atail}$ (SEQ ID NO: 19)

Biotin-ctc gag taa tac gac tca cta ta<u>G</u> AAA GAC GCG CAT TTG TTA TCA

TCA TCC CTG GGA AAG CGA GGC TTT CCC TGG CCA CTC ACG

AGT GGC C *aaa aaa aaa aaa aaa*

(T7 promoter—bold; Transcriptional start site—capital and underlined; MicA$_{stab}$—capitals (68 nt); polyA$_{(A\ tail)}$—italics (15 nt)).

Preparation of DNA-Template Slides

Using either home-prepared streptavidin-spotted slides (see below) or commercially available streptavidin-coated slides (Microsurfaces), ~10 µl of 200 nM Biotin-DNA template in phosphate-buffered saline (PBS) was spotted onto the streptavidin. Slides were incubated at 37° C. in a humidified petri dish for ~30 minutes. Slides were washed ~3× with ~5 ml PBST (PBS with 0.5% Tween), ~1× with H$_2$O and air dried.

Alternatively, NHS-activated slides were treated with 80 mM PDEA in 0.1M sodium borate pH8.5 for 30 minutes to produce reactive disulphide groups. ~10 µl of 200 nM Thiol-DNA template in phosphate-buffered saline (PBS) was spotted onto the activated slide. Slides were incubated at 37° C. in a humidified petri dish for ~30 minutes. Slides were washed ~3× with ~5 ml PBST (PBS with 0.5% Tween), ~1× with H$_2$O and treated with 50 mM cysteine and 1 M NaCl in 0.1 M sodium acetate pH 4 for ~30 minutes to deactivate excess reactive groups.

Preparation of RNA-Binding Slides

1) Immobilization of Tobramycin or Streptavidin to Slides

~10 µl spots of 5 mM tobramycin or 16.6 µM streptavidin in PBS were pipetted onto NHS-activated slides (Schott Nexterion Slide H). The slides were incubated at 37° C. in a humidified petri dish for ~1 hour. The slides were washed ~3× with ~5 ml PBST (0.5% Tween) and ~1× with H$_2$O. The remainder of the NHS-activated surface was blocked with ethanolamine. ~5 ml of 50 mM ethanolamine-HCl was used to cover the slides and they were incubated at room temperature for ~1 hr. The slides were washed ~3× with ~5 ml PBST (0.5% Tween), 1× with H$_2$O and dried in air.

2) Immobilization of Poly-dT 25-mer poly-dT (Invitrogen) was chemically synthesised with a 5' Biotin, re-suspended in PBS at 10 µM and aliquots slide-immobilised in the same way as for the Biotin-DNA templates, detailed above.

RNA Synthesis Using the 'Sandwich Print Set-Up' and Subsequent Slide Visualisation 150 µl of MegaScript T7 in vitro transcription mix (Applied Biosystems, California, USA), sometimes including 0.05 mM Cy3 or Cy5 UTP to Cy-label the RNA, was pipetted over the RNA-binding slide. The DNA-template slide was then placed on top so that the spots of RNA-binding molecule and DNA-template were lined up (although the RNA-binding slides which are completely coated with RNA-binding molecule immobilised do not require specific alignment). In all cases the DNA-template and RNA-binding slides both face inwards. A small piece of parafilm at the ends of the slides was used as a spacer to prevent the slide surfaces from coming into direct contact. The arrangement of the two slides is shown in FIG. 1.

Following incubation at 37° C. for ~1-4 hrs, the slides were separated and the in vitro transcription mix was recovered from the slide surface using a pipette. The DNA template slide was washed ~3× with ~5 ml PBS, ~1× with ~5 ml H$_2$O and air dried. The RNA-binding slide was washed ~3× with ~5 ml PBS, ~1×~5 ml H$_2$O and air dried. Cy-labelled RNA was visualized at 532 nm for Cy3 or 639 nm for Cy5. For unlabeled RNA, the RNA-binding slide was stained by covering the slide with ~5 ml SYBR gold (Invitrogen, Paisley, UK; 5 µl of SYBR gold in ~25 ml PBS) for 10 minutes and visualised with a UV transilluminator.

Results

'Sandwich Print' Set-Up

The general experimental set-up arrangement used to conduct the 'sandwich print' studies is as shown in FIG. 1. RNAs containing different RNA-tags were synthesised from the DNA templates on the DNA-template slide. Through these RNA-tags, the synthesised RNAs bind to the RNA-binding molecules immobilised to the RNA-binding slide directly facing the DNA-template slide. For example, when the tobramycin aptamer was used as the RNA-tag, corresponding biotin-DNA template was immobilised in spots on a streptavidin-slide to create the DNA-template slide whilst tobramycin was covalently immobilised to an NHS-activated slide in spots to create the RNA-binding slide. The two slides were set-up to face each other, with the DNA-template spots aligned with the tobramycin spots (although the RNA-binding slide can be completely tobramycin-coated, removing the need for such alignment). Alternatively, when the streptavidin aptamer was used as the RNA-tag, the DNA-template slide was created by immobilising thiolated-DNA template to a NHS-activated slide in spot format or immobilising biotin-DNA template to streptavidin-spotted slides. For the RNA-binding slide, streptavidin spotted or coated slides were used and set-up facing the DNA-template slide, spots aligned as required. Similarly, when the polyA-tail was used as the RNA-tag, corresponding biotin-DNA template was immobilised in spots on a streptavidin slide to create the DNA-template slide. The RNA-binding molecule, Biotin-poly-dT (25mer), was similarly immobilised to a streptavidin slide to create the RNA-binding slide. The two slides were similarly arranged facing each other with spots aligned as required.

Preparation of DNA Templates

Agarose gel electrophoresis stained with ethidium bromide was used to analyse the DNA templates prior to slide-immobilisation to confirm products of the correct size had been synthesised. FIG. 2 shows an example of successful synthesis of a DNA template, namely, Biotin-EV71-IRES$_{TobApt}$ DNA template.

RNA Synthesis (Sandwich Printing)

The inventor confirmed that RNA of the correct length had been synthesized during the 'sandwich print' process by urea polyacrylamide gel electrophoresis of the 'sandwich print' in vitro transcription solution following incubation for 1-4 hours.

Confirmation of successful RNA 'sandwich printing' is shown in FIG. 3 where EV71-IRES$_{TobApt}$ RNA, synthesized from immobilised Biotin-EV71-IRES$_{TobApt}$ DNA (immobilized on the streptavidin coated DNA slide), bound to immobilised tobramycin (on the facing RNA-binding slide). The RNA was stained with SYBR gold and visualized under UV. Tobramycin-bound EV71-IRES$_{TobApt}$ RNA was still detected following 3 washes with PBS (FIG. 4), indicating the RNA to be stably bound to the tobramycin surface. EV71-IRES lacking the tobramycin aptamer failed to bind to the tobramycin slide.

To demonstrate that this method is successful for a range of RNA molecules of varying sizes and functions, a selection of RNA molecules, with and without tobramycin aptamers, were tested for 'sandwich printing' in a four spot array format. The mRNA, HapR, and small non-coding RNAs (sRNAs), Qrr1, MicA, as well as a mutated sRNA, M-S, were tested. These RNAs range from ~75-100 nt in size, each with a linker of ~20 nt and TobApt of 40 nt. Each RNA only bound to the tobramycin RNA-binding slide when incorporating the tobramycin aptamer, with the control RNAs, lacking the tobramycin aptamer, failing to bind (FIGS. 5 and 6). Similarly, the 623 nt large EV71-IRES$_{TobApt}$ RNA with a 83 nt linker prior to the TobApt as well as the smaller 25 nt U1$_{TobApt}$ RNA with 20 nt linker prior to the TobApt were both seen to be bound to tobramycin following 'sandwich printing' (FIG. 7).

Whilst a number of different linkers between the RNA of interest and RNA-tag have been used, HapR$_{TobApt}$+/−a linker between the HapR and TobApt has also been tested (data not shown). Both HapR$_{TobApt}$+/−a linker were seen to bind to the RNA-binding slide following 'sandwich print'.

To demonstrate that the 'sandwich print' method is applicable to any RNA aptamer interaction, RNA incorporating a streptavidin aptamer (SAApt) as the RNA-tag was tested for binding to a streptavidin RNA-binding slide. FIG. 8 shows the RNA MicA+/−streptavidin aptamer following 'sandwich print'. Only the MicA$_{SAApt}$, incorporating the stretpavadin aptamer, bound to the streptavidin RNA-binding slide. The MicA control, lacking the aptamer, failed to bind. RNAs U1$_{SAApt}$ and Qrr1$_{SAApt}$, of 25 and 99 nt respectively, both incorporating a 26 nt linker and 44 nt streptavidin aptamer, bound to the streptavidin RNA-binding slide following 'sandwich print' (FIG. 9).

To demonstrate that RNA's can be 'sandwich printed' on the same array slide via different RNA tags, RNAs incorporating either a TobApt or SAApt were 'sandwich printed' from their corresponding DNA template onto an RNA-binding slide opposite spotted with the corresponding RNA binding molecules of tobramycin and streptavidin. FIG. 10 shows the RNAs M-S$_{TobApt}$ and M-S$_{SAApt}$ following 'sandwich print'. The M-S$_{TobApt}$ bound to the tobramycin spot of the RNA-binding slide whilst the M-S$_{SAApt}$ bound to the streptavidin spot of the RNA-binding slide.

Whilst RNA aptamers represent one form of RNA-tag that will bind tightly to a specific partner molecule, a complementary RNA-DNA base-pairing interaction can also be used to specifically bind RNA to a RNA-binding slide. To demonstrate this, the RNAs Qrr1 and M-S with 15-mer polyA tails were tested using the 'sandwich print' method for binding to immobilised 25mer poly-dT on the RNA-binding slide. FIG. 11 shows successful binding of the RNAs to the poly-dT RNA-binding slide.

REFERENCES

Gao et al., (2003) Nucleic Acids Research, 31, e143
Kim et al., (2006) JACS 128, 12076-12077
Lee et al., (2006) (Corn group) Langmuir 22, 5241-5250
Sendroiu et al. (2011) Journal of the American Chemical Society, 133, 4271-4273;
Wahlestedt C. (2006) Drug Discovery Today, 11, 503-08

The invention claimed is:

1. A method of immobilising a plurality of RNA molecules onto a surface of a support comprising:
   i) providing a first support that is a continuous planar surface on which a plurality of DNA molecules are immobilised, wherein each DNA molecule encodes an RNA molecule comprising a binding molecule;
   ii) providing a second support that is a continuous planar surface on which a plurality of binding partners for interacting with the binding molecules are immobilised;
   iii) arranging the first and second supports such that the surfaces displaying the immobilised DNA molecules and binding partners are in close proximity and substantially face each other, and contacting the DNA molecules immobilised on the surface of the first support with transcription reagents such that the surfaces of the first and second support are in contact with the transcription reagents; and
   iv) carrying out a transcription reaction between the first and second support to generate the RNA molecules, wherein the RNA molecules are directly immobilised onto the surface of the second support via an interaction between the binding molecule of the RNA molecule and the binding partner on the surface of the second support.

2. The method according to claim 1, wherein the DNA molecules comprise a promoter sequence operably linked to a sequence encoding the RNA molecule.

3. The method according to claim 2, wherein the promoter sequence is specific for T7 RNA polymerase.

4. The method according to claim 1, wherein the binding molecule is an RNA aptamer.

5. The method according to claim 4, wherein the RNA aptamer is a tobramycin-binding RNA aptamer or a streptavidin-binding RNA aptamer.

6. The method according to claim 5, wherein the binding partner immobilised on the surface of the second support is tobramycin or streptavidin.

7. The method according to claim 1, wherein the DNA molecule is immobilised onto the surface of the first support using biotin and streptavidin.

8. The method according to claim 1, wherein the plurality of DNA molecules have the same sequences such that the RNA molecules have the same sequences.

9. The method according to claim 1, wherein the plurality of DNA molecules have different sequences such that the RNA molecules have different sequences.

10. The method according to claim 1, wherein the RNA molecules encoded by the plurality of DNA molecules comprise the same binding molecule.

11. The method according to claim 1, wherein the RNA molecules encoded by the plurality of DNA molecules comprise different binding molecules.

12. The method according to claim 1, wherein the plurality of binding partners are the same.

13. The method according to claim 1, wherein the plurality of binding partners are different.

14. The method according to claim 1, wherein the first support is in an array format.

15. The method according to claim 1, wherein the second support is in an array format.

16. The method according to claim 1, wherein the step of arranging the first and second supports further comprises providing at least one spacing element to separate the surfaces of the first and second support such that the surfaces are not in direct contact.

17. A kit for carrying out the method claim 1, comprising: i) a first support that is a continuous planar surface comprising a plurality of DNA molecules immobilised thereon, wherein each DNA molecule encodes an RNA molecule comprising a binding molecule; ii) a second support that is a continuous planar surface for immobilising the RNA molecules encoded by the plurality of DNA molecules thereon, wherein a plurality of binding partners for interacting with the binding molecules are immobilised on the surface of the second support; and iii) transcription reagents, wherein the first and second supports can be arranged such that the surfaces displaying the immobilised DNA molecules and binding partners are in close proximity and substantially face each other.

18. The kit according to claim 17, further comprising means for securing the first and second supports such that the surfaces displaying the immobilised DNA molecules and binding partners are in close proximity and substantially face each other.

19. The kit according to claim 17, wherein the first support is in an array format.

20. The kit according to claim 17, wherein the second support is in an array format.

21. The kit according to claim 17, further comprising at least one spacing element for separating the surfaces of the first and second support such that, in use, the surfaces are not in direct contact.

22. The method according to claim 1, wherein the binding molecule is a nucleotide sequence and the binding partner is an oligonucleotide that is complementary to the nucleotide sequence of the binding molecule.

23. The method according to claim 1, wherein the method further comprises translating the immobilized RNA molecules to produce protein molecules.

24. The method according to claim 23, wherein the protein molecules are immobilized onto a third support following translation.

25. The kit according to claim 17, further comprising a third support having a surface for immobilizing the protein molecules encoded by the RNA molecules thereon.

26. The kit according to claim 25, further comprising translation agents.

27. The method according to claim 1, wherein the binding molecule is located at the 3' end of the RNA molecule such that only the full length RNA molecule comprises the binding molecule.

28. The method according to claim 1, wherein the surfaces of the first and second supports are separated by a gap of about 10-200 µm.

29. The method according to claim 1, wherein the DNA molecules immobilised on the surface of the first support are contacted with transcription reagents such that the surfaces of the first and second support are in contact with the transcription reagents in a single continuous transcription mix.

* * * * *